United States Patent
Kim et al.

(10) Patent No.: US 6,787,621 B2
(45) Date of Patent: Sep. 7, 2004

(54) VINYL GROUP-CONTAINING DIARYLETHENE AND POLYMER THEREOF HAVING EXCELLENT OPTICAL PROPERTIES

(75) Inventors: Eunkyoung Kim, Daejeon (KR); Song Yun Cho, Kangwon-do (KR); Min Ja Yoo, Boryung-shi (KR); Kwang-Hyun Ahn, Choongchungnam-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 10/246,414

(22) Filed: Sep. 19, 2002

(65) Prior Publication Data

US 2003/0130456 A1 Jul. 10, 2003

(30) Foreign Application Priority Data

Sep. 21, 2001 (KR) ........................................ 2001-58753

(51) Int. Cl.[7] ............................. C08G 18/40; G03C 1/73
(52) U.S. Cl. .................... 526/204; 526/281; 526/292.2; 526/292.5; 526/292.7; 548/469; 430/496
(58) Field of Search ................................. 526/204, 281, 526/292.2, 292.5, 292.7; 548/469; 430/496, 962; 525/380

(56) References Cited

U.S. PATENT DOCUMENTS

2003/0118924 A1 * 6/2003 Kim et al. .................... 430/19

FOREIGN PATENT DOCUMENTS

JP 6240242 8/1994

OTHER PUBLICATIONS

Takashi Yoshida, et al., "Refractive Index Changes In Photochromic Diarylethene Derivatives In Polymethylmethacrylate Films", *Journal of Photochemistry and Photobiology A: Chemistry*, vol. 95, pp. 265–270, (1996).

Akira Hirao, et al., "Anionic Polymerization of Monomers Containing Functional Groups 9. Anionic Polymerizations of 4–Vinylphenyl Methyl Sulfide, 4–Vinylbenzyl Methyl Sulfide, and 2–(4'–Vinylphenyl)ethyl Methyl Sulfide", *Macromolecules*, vol. 30, pp. 3728–3731, (1997).

Masahiro Irie, et al., "Photochromic Diarylethenes with Intralocking Arms", *Journal American Chemical Society*, vol. 116, pp. 9894–9900, (1994).

\* cited by examiner

*Primary Examiner*—James J. Seidleck
*Assistant Examiner*—Olga Asinovsky
(74) *Attorney, Agent, or Firm*—Finnegan, Henderson, Farabow, Garrett & Dunner, L.L.P.

(57) ABSTRACT

Vinyl group-containing diarylethene monomers and photochromic polymers made there from. The diarylethene monomers may be suitable for controlled polyermerization. Polymers formed from the diarylethene monomers may have optical properties such as, for example, optical signal control properties, photochromic properties, and/or optical reflectivity properties.

6 Claims, 1 Drawing Sheet

VINYL GROUP-CONTAINING DIARYLETHENE AND POLYMER THEREOF HAVING EXCELLENT OPTICAL PROPERTIES

FIELD OF THE INVENTION

The present invention relates to a vinyl group-containing diarylethene monomer expressed by formula (1) and a polymer thereof having optical properties. More particularly, it relates to a vinyl group-containing diarylethene monomer of formula (1), suitable for controlled polymerization and a polymer thereof having excellent optical properties such as control characteristics of optical signal, photochromic characteristics, and control characteristics of optical reflectivity by introducing the diarylethene monomer of formula (1) into the polymer chain,

(1)

wherein $Z^1$ and $Z^2$ are independently cyano group or attached form of 4–6-membered ring optionally substituted with one or more fluoro atoms; and $Ar^1$ and $Ar^2$ are independently

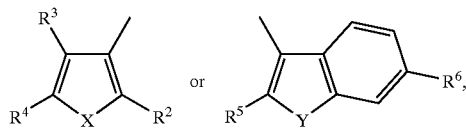

where X and Y are O, S, NH or N—$CH_3$; $R^2$ and $R^5$ are optionally substituted $C_1$–$C_3$ alkyl; $R^3$ is H, F or optionally substituted $C_1$–$C_3$ alkyl; and $R^4$ and $R^6$ are independently H, $CH_3$, C(=O)$CH_3$, isoxazole, vinyl, C(=O)—$Ar^3$—CH=$CH_2$, C(=O)-$Ar^4$, or N($Ar^5$)$_2$, where $R^4$ or $R^6$ of either $Ar^1$ and $Ar^2$ should be vinyl or C(=O)—$Ar^3$—CH=$CH_2$ and $Ar^3$, $Ar^4$ or $Ar^5$ should be optionally substituted benzene or thiophene.

BACKGROUND OF THE INVENTION

Demand in photochromic lenses, high density photochromic recordings, high speed optical communications, and large scale integrated circuits has been dramatically increased with development of technologies in shielding of sun light, optical signal processing, optical transfer, optical filter and the like. The optical devices contain photochromic and photorefractive materials which change color and transparency with light irradiation and are capable of signal recording and/or reproducing with laser irradiation. Among organic photochromic materials, diarylethene compounds have excellent thermal stability and repetitive durability, thus leading to proposals for their use in optical applications such as optical devices, optical recordings and the like.

It has been reported that diarylethene compounds have high thermal stability and photochromism so that they are useful for functioning in a polymer film [Refractive index changes in photochromic diarylethene derivatives in poly-methylmethacrylate films, *Journal of Photochemistry and Photobiology A: Chemistry*, Volume 95, Issue 3, May 10, 1996, Pages 265–270, Takashi Yoshida, Koichi Arishima, Fumihiro Ebisawa, Mitsutoshi Hoshino, Ken Sukegawa, Atsushi Ishikawa, Tatsuya Kobayashi, Makoto Hanazawa and Yukio Horikawa]. However, when the diarylethene compounds are used for preparing polymer films, it is difficult to obtain homogeneous thin film due to insufficient compatibility of diarylethene compounds with polymer resin and sufficient photochromic effect due to the agglomeration among photochromic materials. In addition, when a large amount of diarylethene compound is used to enhance the efficiency, the obtained film is not clear and phase separation may occur with storing for a long period time because the diarylethene compound is dissolved out or forms microcrystals. Therefore, it is unreliable and lack of storage stability for long term use.

In order to be free of these defects, Japan Patent Publication No. 6-240242 discloses polymeric photochromic composition comprising a polymer having methacryl-base diarylethene groups bonded to a polymer chain. However, the methacryl-base diarylethene compounds have low reactivity during the polymerization and do not bond efficiently to the polymer chain because it is difficult to control the blocks, thus being inappropriate in the preparation of the polymer having hyper-branches.

Accordingly, the necessity of developing monomers having high reactivity and polymers using thereof is keenly demanded.

SUMMARY OF THE INVENTION

Accordingly, an object of the present invention is to provide a diarylethene monomer of formula (1) capable for the preparation of a polymer having excellent optical properties through anionic polymerization, cationic polymerization or radical polymerization.

Another object of the present invention is to provide a polymer having excellent optical properties such as control characteristics of optical signal, photochromic characteristics, and control characteristics of optical refractivity as well as transparence without phase separation.

Further object of the present invention is to provide a composition comprising 0.01–99.8 weight % of a diarylethene monomer of formula (1), 0–99.8 weight % of a comonomer, and 0.19–5 weight % of a polymerization initiator, thus capable for thin layer-coating on the various structure of substrates.

BRIEF DESCRIPTION OF THE DRAWINGS

The above and other objects and features of the present invention will become apparent from the following description of the invention, when taken in conjunction with the accompanying drawing, in which.

DETAILED DESCRIPTION OF THE INVENTION

Figure 1:
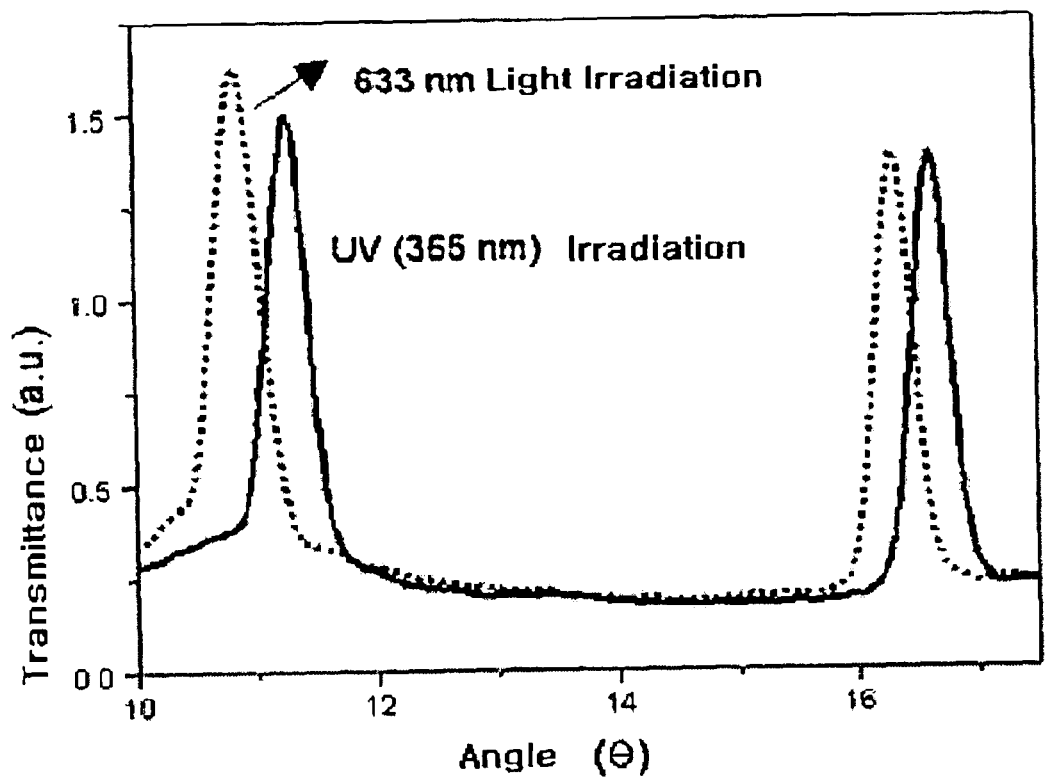
FIG. 1 represents the peak shift in the angle spectra for VMBTF6-styrene block copolymer film upon excitation with UV/Vis light.

The present invention provides a diarylethene monomer of the following formula (1),

(1)

wherein $Z^1$, $Z^2$, $Ar^1$ and $Ar^2$ are as previously defined.

Especially preferred compounds of the formula (1) include:
(1a)
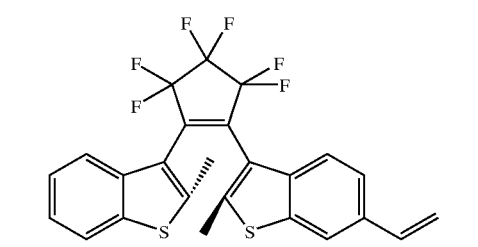
(1b)
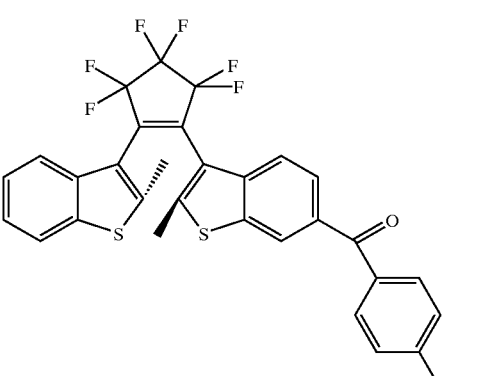
(1c)
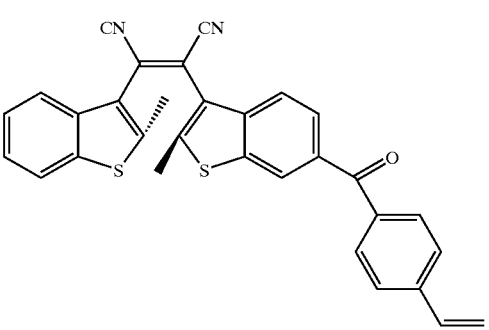
(1d)
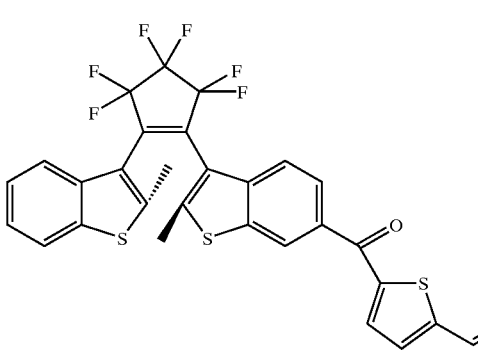
(1e)
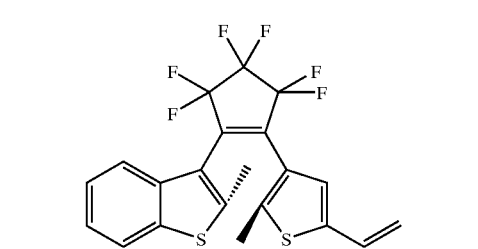
(1f)
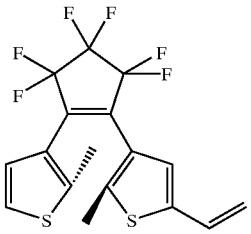
(1g)
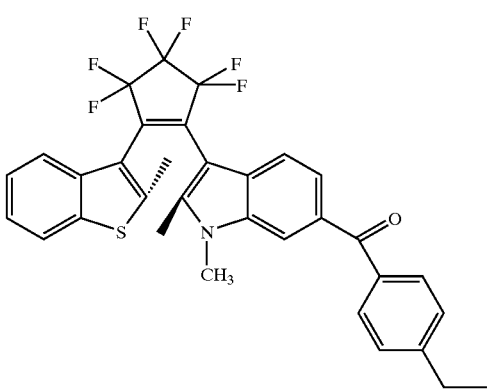
(1h)
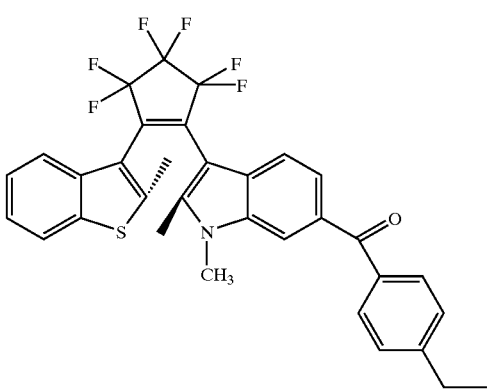
(1i)
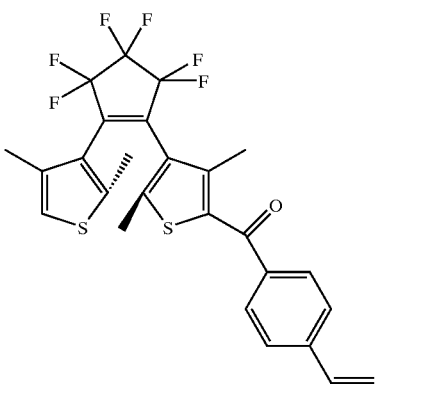
(1j)
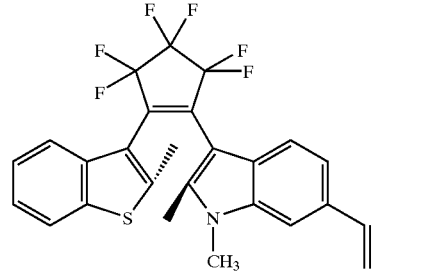

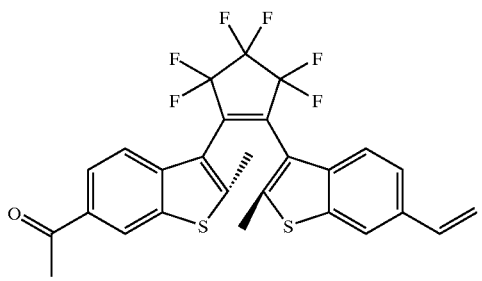

(1k)

These diarylethene monomers of the formula (1) may be prepared from known diarylethene compound. For example, 1-(6'-vinyl-2'-methylbenzo[b]thiophene-3'-yl)-2-(2"-methylbenzo[b]thiophene-3"-yl)hexafluorocyclopentene (VMBTF6) is prepared by reacting 1-(6'-formyl-2'-yl)-2-(2"-methylbenzo[b]thiophene-3"-yl) hexafluorocyclopentene (FMBTF6), methyltriphenylphosphonium iodide and n-butyllithium through the known method disclosed in Irie, M., Miyata, O., Uchida, K., Eriguchi, T., JACS, 9894(1994) in 85%.

A polymer having optical properties of the present invention is prepared by using a composition comprising 0.01–99.8 weight % of a diarylethene monomer of formula (1), 0–99.8 weight % of a comonomer and 0.19–5 weight % of a polymerization initiator. Examples of the polymer having optical properties include diarylethene polymers, diarylethene random copolymers, and diarylethene block copolymers. Examples of the known comonomer include styrene or its derivatives, hydrocarbons substituted with vinyl, acryl, or methacryl group, and fluorinated compounds substituted with vinyl, acryl, or methacryl group. Examples of the polymerization initiator include alkyl lithium, 2,2,6,6-tetramethyl-1-piperdinyloxy nitroxide (TEMPO) or its derivatives represented as $CR_1R_2R_3COR_4$, (wherein $R_1$ is a persistent radical but cleaved from carbon atom at 100–160° C. so that it can have the same function as TEMPO; $R_2$ is a hydrogen atom; $R_3$ a hydrogen atom, methyl, phenyl or p-nitrophenyl; $R_4$ is an ethoxy, 4-benzyl-2-oxazolidone-3-yl, aryloxy, or 2-oxazolidone-3-yl), radical initiators such as 2,2-azobisisobutyronitrile (AIBN), benzoyl peroxide (BPO), camphorquinone [2,3-bornanedione; 1,7,7-trimethylbicyclo (2,2,1)heptane-2,3-dione], 4-(2-hydroxyethoxy)-phenyl-(2-hydroxy-2-methylpropyl)ketone, cationic initiators such as metal halide (e.g., $TiCl_4$ and $SnCl_4$) and mixtures thereof. Since among these initiators, alkyl lithium, TEMPO or its derivative, or a cationic initiator such as metal halide is useful for the preparation of polymers requiring controls in the length of blocks, molecular weight, and molecular weight distribution, it is applicable to prepare photoactive polymers having controlled length of photochromic block and molecular weight and narrow molecular weight distribution in the polymer prepared from the diarylethene monomer of formula (1). Other additives, used by one having ordinary skilled in the art, such as a photosensitizer and molecular weight distribution controller may be arbitrarily incorporated.

For example, VBMBTF6 (1 equivalent) of formula (1b) and styrene (3 equivalent) are dissolved in toluene and ethyl α-tempo-phenyl acetate is added thereto. The mixture is reacted at 150° C. for 48 hours and then cooled down to room temperature, and methanol was added to the mixture, to provide a random copolymer having VBMBTF6 and styrene (a mole ratio of 1:3). The resulted random copolymer has a glass transition temperature of 120° C., a weight average molecular weight ($M_w$) of 11,500, a narrow molecular weight distribution of 1.21, excellent solubility in an organic solvent, and excellent photochromism.

A diarylethene monomer of formula (1) and an initiator are reacted to provide living polymer anions or living polymer radicals, which are further reacted with a comonomer having unsaturated functional groups, to produce a block copolymer having an appropriate length of diarylethene block and comonomer block. For example, VBMBTF6 (1 equivalent) of formula (1b) is dissolved in toluene. Ethyl α-tempo-phenylacetate as an initiator is added thereto and the mixture is reacted at 150° C. for 12 hours, followed by cooling down to a room temperature. Styrene (3 equivalents) is added to the reaction mixture and further reacted at 150° C. for 64 hours. After the reaction mixture is cooled down, and methanol was added to the mixture, to separate a block copolymer of formula (2) having VBMBTF6 and styrene (a mole ratio of 1:3). The resultant block copolymer has a weight average molecular weight ($M_w$) of 11,700, a molecular weight distribution of 1.25, and excellent solubility in organic solvents, thus capable of being used for photochromic materials,

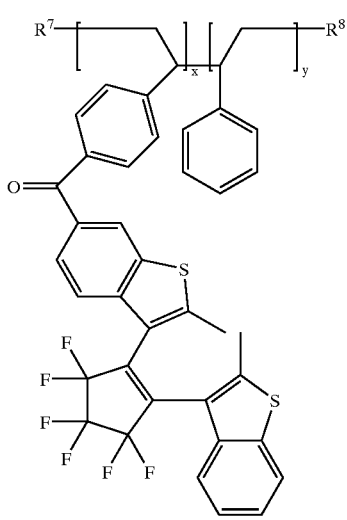

(2)

wherein x:y=1:3; $R^7$ and $R^8$ are derived from each initiator, $R^9S$, $R^{100}$ or H, where $R^9$ and $R^{10}$ are optionally substituted $C_1$–$C_{20}$ alkyl or alkylbenzene.

In the preparation of the block copolymer, the length of diarylethene blocks may be easily adjusted by controlling the mole ratio of a comonomer. Since the block copolymer has different photochromic characteristics such as photochromic efficiency, refractive index changes with light, etc. from the random copolymer, it is possible to prepare polymers having excellent optical properties by controlling the length of blocks and structure of comonomers.

The random copolymer may be also prepared by using a comonomer having unsaturated functional groups with a diarylethene monomer of formula (1). Examples of the comonomer having unsaturated functional groups include cyclopentadiene, styrene or its derivative, butyl methacrylate, norbornene, isobutene, indene, N-vinylcarbazole, pyrene, 4-vinylphenylalkyl sulfate [Akira Hirao, Hideki Shione, Takashi Ishizone, and Seiichi Nakahama, Macromolecules, 30 (13), 3728–3731, 1997].

The diarylethene monomer of formula (1) is used to provide a transparent photochromic thin film by polymerizing to diarylethene polymer or copolymer, dissolving the result polymer in solvent, coating on the surface of substrate such as glass, quartz, or silicon wafer, and drying. As an example, a transparent thin film having excellent adhesion and photochromic property is prepared by dissolving a block copolymer of formula (2) in cyclohexanone, reacting at room temperature for 1 hour, spin-coating on the surface of quartz and drying in the oven at 50° C. for 12 hours. When light having 300 nm of wavelength or higher is irradiated, color of the film has been changed to red and maintained the red color in a darkroom. When this process is repeated, no phase separation is occurred and a refractive index change was 0.005 with the light irradiation of 365 nm and He—Ne laser. The refractive index change is useful information to apply in refractive index changing elements, display materials and optical recordings.

In addition, a thin film is obtained by mixing a diarylethene monomer, a comonomer having unsaturated functional group and an initiator, irradiating with heat or light, and coating on the surface of substance such as glass, quartz, and silicon wafer. The initiator to be used in the present invention is chosen from 2,2-azobisisobutyronitrile (AIBN), benzoyl peroxide (BPO), diisopropyl peroxydicarbonate (IPP), t-butylhydroperoxide (TBPO), heat-curing initiators, and light-curing initiators such as camphorquinone (Aldrich), 4-(2-hydroxyethoxy)-phenyl-(2-hydroxy-2-methylpropyl)ketone (Irgacure 2959, Ciba-Geigy) and mixtures thereof. A photosensitizer may be arbitrarily incorporated. Examples of the comonomers include styrene or its derivatives, butylmethacrylate, di(ethylene glycol) dimethacrylate, glycidyl methacrylate, tri(ethylene glycol) dimethacrylate, tetra(ethylene glycol) dimethacrylate, butanediol dimethacrylate, hydroxyethyl methacrylate (HEMA), hexamethylene dimethacrylate, perfluoroalkyl acrylate, acrylamide, bisphenol A dimethacrylate, 2,2-bis(4-methacryloyloxyethoxy-3,5-dibromophenyl)propane, 2,2-bis(4-methacryloyloxyethoxyphenyl)propane, 2,2-bis(4-methacryloyloxydiethoxyphenyl)propane, 2,2-bis(4-methacryloyloxytriethoxyphenyl)propane, 2,2-bis(4-methacryloyloxypentaethoxyphenyl)propane, methoxy poly (ethylene glycol)methacrylate, bis-4-vinylbenzyl ether, bis-4-vinylbenzyl sulfide, 1,2-(p-vinylbenzyloxy)ethane, 1,2-(p-vinylbenzylthio)ethane, bis-(p-vinylbenzyloxylethyl) sulfide,

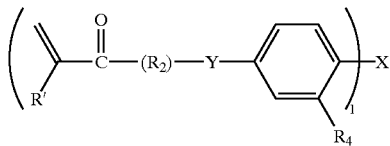

(where X is a hydrogen atom, —S—, —$SO_2$—, —C(=O)— or —$C(R_1)_m(R_3)_{2m}$—; $R_1$ is a hydrogen atom or methyl; $R_2$ is —$[C(R_1)_m(R_3)_{2-m}$—$C(R_1)_m(R_3)_{2-m}$—$Z]_n$—; $R_3$ is the same as $R_1$ or alkyl substituted with F, Cl, or Br; $R_4$ is the same as $R_1$, —C(=$CH_2$)—$CH_3$; l is an integer of 1 to 2, m is an integer of 0 to 2, n is an integer of 0 to 20; Y is —C(=O)—O—, —O—C(=O)—O—, —$SO_2$, —S—, —C(=O)—, —C(=O)—NH—$C(R_1)_m(R_3)_{2-m}$— or a bond; Z is —$C(R_1)_m(R_3)_{2-m}$—, —S—, or —O—), norbornene, isobutene, indene, Further comonomers include $CH_2$=CH—$CH_2(CF_2)_nCH_2CH$=$CH_2$, $CH_2$=CH—$CH_2(CF_2)_nR$ (where, n is an integer of 1 to 50, R is $C_1$-$C_{20}$ alkyl substituted with F or H).

Further, the present invention provides a polymeric composition comprising 0.01–99.8 weight % of a diarylethene monomer of formula (1), 0–99.8 weight % of at least one comonomer having unsaturated functional group chosen from styrene, vinyl, methacry and acryl compound and 0.19–5 weight % of a polymerization initiator. The polymeric composition of the present invention is useful to produce optical lens, film, coating layer, and the like through heat or light curing. These compounds may be commercialized by Aldrich or other companies or prepared by known methods.

Other additives such as aliphatic unsaturated compound, binder resin, and organic solvent may be incorporated to control the thickness and/or viscosity of thin films. And further, catalyst to activate the polymerization or UV absorber, or coloring resistant may be arbitrarily incorporated.

The obtained composition can be coated on the substrate such as glass, ITO, silicon wafer and the like or molded in various materials through light or thermal curing. The thermal curing is employed for 3–48 hours depends on the amount of composition and initiator. For example, if benzolyperoxide (BPO) is used, the curing condition is preferred to irradiate with UV lamp, UV irradiator or Xenon lamp at −20 to 120° C. for 30 seconds to 2 hours.

For example, a composition comprising diarylethene monomer (10 weight %) of formula (1b), fluoro dimethacrylate (88 weight %) and Irgacure 184 (2 weight %) is polymerized with UV light at room temperature for 5 minutes to provide a thin film having a thickness of 25 μm, a refractive index of 1.58 and a pencil hardness of 8H. The obtained thin film has photochromism and refractive index change of 0.002 with UV/visible light irradiation and is also not decomposed for a year at room temperature.

Other known photochromic compounds such as azobenzenes, spiro benzopyranes, nitrooxazines, cromenes and the like may be added in the range of from 0.5 to 50 weight % to the thin film composition.

The photochromic thin film of the present invention has excellent transparency, photochromism, refractive index changes with light, and high color contrast. Consequently, the photochromic products prepared from the photochromic thin film also have excellent transparence, photochromism, refractive index changes, hardness, thermal stability, and durability, thus effectively suitable for optical applications such as optical lenses, optical filters, imaging devices, large scale integrated devices, optical switches, optical disks and optical recording mediums.

The photochromic thin film of the present invention changes color with UV/visible light radiation and maintains its photochromism without decomposing when it is kept at room temperature for a year. Thus, the photochromic products prepared from the photochromic thin film such as plastic lenses, photochromic films, photochromic imaging films change its color to red with UV irradiation and to colorless with visible irradiation. Especially, when it is exposed to sun light, it is colored to be suitable for shielding glasses for sun light, automotive windows, UV sensors and the like.

For photochromic imaging, which is direct recording on the photochromic plates by using light, diarylethene-containing composition is coated on the surface of substrate such as wafer, transparent plastic plate, glass and the plate coated with ITO or metal layer, by using UV/VIS light. For example, when the photochromic thin film covered with a patterned mask is irradiated by He—Cd laser (wavelength in the UVe region) the mask pattern is transferred on the thin film. Or after the photochromic film is colored with UV light irradiation, it is further recorded by direct or near-field method using a He—Ne laser (wavelength in the visible region). This recording characteristics is readable by eye or using a microscope, an optical microscope, a fluorescence microscope, a confocal microscope, AFM, or IR light. The records can be completely erased and reproduced with UV or VIS light and it stays for 1 year or longer.

The following Preparation Examples and Examples are intended to further illustrate the present invention without limiting its scope. Testing methods employed in measuring properties in the Examples are as follows.

[Method]
(1) Thickness: measured by α-Step 200
(2) Photochromism: measured by UV/VIS spectrophotometer
(3) Refractive index and photo induced refractive index change: determined using a prism coupler with 830 nm laser

PREPARATION EXAMPLE 1

Preparation of Ethyl α-tempo-phenylacetate Initiator

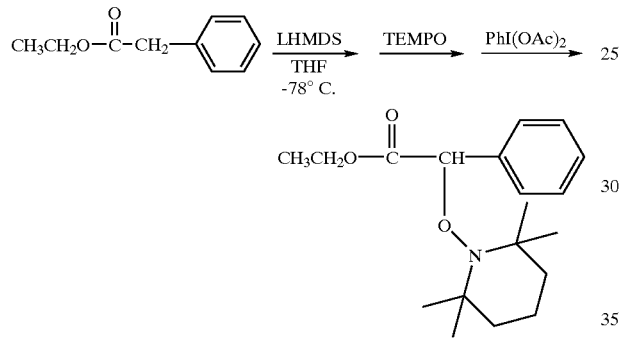

Ethyl phenylacetate (200 mg, 1.218 mmol) was added in dry THF (10 ml) in 100 ml round-bottom flask and the temperature was kept at −78° C. Lithium bis(trimethylsiliyl) amide (Aldrich, LHMDS; 1M solution in THF, 1.5 ml, 1.462 mmol) was added slowly to the reaction mixture. The reaction mixure was stirred at −78° C. for 3.5 hours and then at room temperature for 2 hours. The reaction was ceased by adding methanol. Solvent and volatile components were evaporated under reduced pressure. The residue was purified by column chromatography on silica gel using hexane and ethyl acetate to obtain the desired product (244.4 mg, yield 76%).

In TLC, $R_f$ was 0.66 (hexane/ethyl acetate =5/1);

$^1$H NMR(CDCl$_3$, 200 MHz) δ7.38-7.19(5H, m), 5.11(1H, s), 4.06–4.00(2H, m), 1.41–0.64(21H, m)

PREPARATION EXAMPLE 2

Preparation of Diarylethene Monomer (FMBTF6)

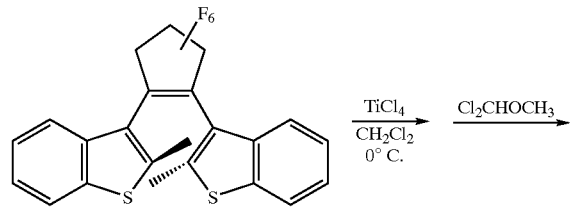

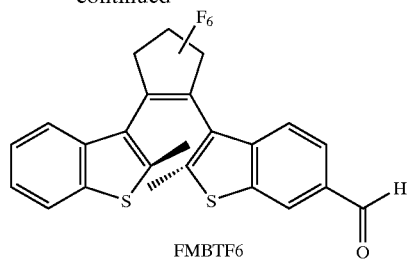

FMBTF6

1,2-Bis(2-methylbenzo[b]thiophene-3-yl) hexafluorocyclopentene(BTF6; 4 g, 8.5 mmol) was dissolved in CH$_2$Cl$_2$(50 mL) and cooled to 0° C. under N$_2$. TiCl$_4$(25.6 mL, 25 mmol) and Cl$_2$CHOCH$_3$(1.2 mL, 12.807 mmol) were added to the reaction mixture and stirred at 0° C. for 10 min and then at room temperature for 5 hours. The reaction was ceased by adding ice-water. The reaction mixture was extracted with water and CH$_2$Cl$_2$ and organic layer was dried over MgSO$_4$ and evaporated to dryness under reduced pressure. The residue was purified with flash column chromatography on silica gel to obtain 1-(6'-formyl-2'-methylbenzo[b]thiophene-3'-yl)-2-(2"-methylbenzo[b]thiophene-3"-yl)hexafluorocyclopentene (FMBTFP; yield 80%).

EXAMPLE 1

Preparation of 1-(6'-vinyl-2'-methylbenzo[b]thiophene-3'-yl)-2-(2"-methylbenzo[b]thiophene-3"-yl)hexafluorocyclopentene(VMBTF6 of Formula 1a)

Methyltriphenyl phosphonium iodide (3.9 g) was dissolved in THF (70 mL) and the temperature of the reaction medium was kept at −78° C. n-Butyl lithium (4.6 mL) was added to the reaction mixture and stirred for 30 min and then at room temperature for 30 min. After the reaction mixture was again cooled to −78° C., 1-(6'-formyl-2'-methylbenzo[b]thiophene-3'-yl)-2-(2"-methylbenzo[b]thiophene-3"-yl)hexafluorocyclopentene (FMBTF6) (4.36 g) prepared by the known method [Irie, M., Miyata, O., Uchida, K., Eriguchi, T., JACS, 9894(1994)] was added and stirred for 10 min. And then the reaction mixture was stirred at room temperature for 2 hours. After the reaction was ceased by adding ice-water, it was extracted with water and ethyl acetate. The organic layer was dried over MgSO$_4$ and evaporated to dryness under reduced pressure. The residue was purified with flash column chromatography on silica gel to obtain VMBTF6(3.51 g, yield 90%).

$^1$H-NMR(CDCl$_3$, 200 MHz) δ2.20(s, 1H), 2.47(s, 1H), 5.25(d, 1H, J=11.02), 5.75(d, 1H, J=17.38), 6.62(dd, 1H, J=10.96, 17.54), 7.20–7.70(m, 7H)

EXAMPLE 2

Preparation of 1-[6'-(hydroxystyl)methyl-2'-methylbenzo[b]thiophene-3'-yl]-2-(2"-methylbenzo[b]thiophene-3"-yl)hexafluorocyclopentene 4-Bromostyrene (0.2 g) was added to Mg(0.027 g) in THF(3 mL) and the reaction mixture was stirred for 2 hours. 1-(6'-Formyl-2'-methylbenzo[b]thiophene-3'-yl)-2-(2"-methylbenzo[b]thiophene-3"-yl)hexafluorocyclopentene (FMBTF6, 0.27 g) prepared by the known method [Irie, M., Miyata, O., Uchida, K., Eriguchi, T., JACS, 9894(1994)] was added and stirred at room temperature for 4 hours. The reaction was ceased by adding 1N HCl and organic parts were extracted with methylene chloride. The organic layer was dried over MgSO$_4$ and evaporated to dryness under reduced pressure. The residue was purified with flash column chromatography on silica gel to obtain 1-[6'-(hydroxystyl)methyl-2'-methylbenzo[b]thiophene-3'-yl]-2-(2"-methylbenzo[b]thiophene-3"-yl)hexafluorocyclopentene (0.304 g, yield 92%).

$^1$H-NMR(CDCl$_3$, 200 MHz) δ 2.18(s, 1H), 2.39(s, 1H), 5.24(d, 1H, J=10.82) 5.69–5.80(br. m, 2H), 6.70(dd, 1H, J=10.82, 11.06), 7.15–7.38(m, 7H), 7.50–7.73(m, 4H)

EXAMPLE 3

Preparation of 1-[6'-(4"'-vinylbenzoyl)-2'-methylbenzo[b]thiophene-3'-yl]-2-(2"-methylbenzo[b]thiophene-3"-yl)hexafluorocyclopentene (VBMBTF6 of Formula 1b)

1-[6'-(Hydroxystyl)methyl-2'-methylbenzo[b]thiophene-3'-yl]-2-(2"-methylbenzo[b]thiophene-3"-yl)hexafluorocyclopentene (1.2 g) obtained in Example 2 was dissolved in toluene (10 mL) and 2,3-dichloro-5,6-dicyano-1,4-benzoquinone (DDQ, 1.13 g) was added and stirred under refluxing condition for 2 hours. The reaction mixture was cooled to room temperature and volatile parts were evaporated to dryness under reduced pressure. The residue was purified with flash chromatography on silica gel to obtain 1-[6'-(4"'-vinylbenzoyl)-2'-methylbenzo[b]thiophene-3'-yl]-2-(2"-methylbenzo[b]thiophene-3"-yl)hexafluorocyclopentene (0.81 g, yield 78%).

$^1$H-NMR(CDCl$_3$, 200 MHz) δ2.27(s, 1H), 2.55(s, 1H), 5.42(d, 1H, J=10.86), 5.91(d, 1H, J=17.58), 6.79(dd, 1H, J=11.06, 14.64), 7.17–7.41(m, 3H), 7.46–8.14(m, 8H)

EXAMPLES 4–6

Other diarylethene monomers in Table 1 were prepared according to Examples 1–3.

TABLE 1

| Category | Starting material | Reaction condition solvent/time/temp. | Yield (%) | $^1$H-NMR |
|---|---|---|---|---|
| Example 4 (formula 1c) | 1) FBTCN, Mg, 4-bomostyrene 2) DDQ | 1) THF/5 h/30° C. 2) toluene/3 h/ 100° C. | 82 | 2.41(3H), 2.67(3H), 5.18(1H), 5.70(1H), 6.62(1H), 7.38–7.5(4H), 7.76–7.9(4H), 8.1–8.2(2H), 8.3(1H) |
| Example 5 (formula 1g) | 1) FNTF6, Mg, 4-bromostyrene 2) DDQ | 1) THF/4 h/25 ° C. 2) toluene/4 h/ 90° C. | 80 | 2.52(3H), 2.54(3H), 3.67(3H), 5.16(1H), 5.70(1H), 6.62(1H), 7.9–7.4(4H), 7.5–7.6(2H), 7.7–7.9(3H), 7.96(2H) |
| Example 6 (formula 1j) | FBTCN, methyltriphenyl phosphonium iodide, n-butyl lithium | Same as Example 1 | 92 | 2.4(3H), 2.6(3H), 5.15(1H), 5.60(1H), 6.6(1H), 7.38–7.5(4H), 8.1–8.29(3H) |

FBTCN:

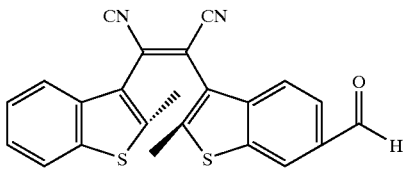

FNTF6:

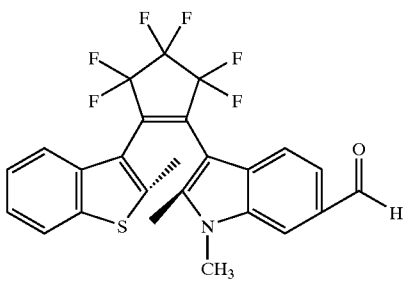

EXAMPLE 7

Preparation of VMBTF6-styrene Random Copolymer

Diarylethene monomer (formula 1a, VMBTF6; 0.950 g) obtained in Example 1 and styrene (0.6 g) were dissolved in toluene (3 mL). Ethyl α-tempo-phenylacetate (0.02 g) as an initiator was added and the reaction mixture was stirred at 150° C. for 48 hours. After the reaction temperature was cooled to room temperature, methanol was added into the reaction mixture. White solid obtained was collected, dried (1.15 g) and identified as a random copolymer having VMBTF6 and styrene (1:3, molar) component. The obtained copolymer has a glass transition temperature of 98° C., a weight average molecular weight of 16000 and a molecular weight distribution of 1.4 and further has excellent solubility in organic solvent so that it was suitable for photochromic elements.

EXAMPLE 8

Preparation of VMBTF6-styrene Block Copolymer

VMBTF6 (0.905 g) prepared in Example 1 was dissolved in toluene (3 mL) and an initiator, ethyl a-tempo-phenylacetate (0.02 g) was added thereto. The reaction mixture was stirred at 150° C. for 48 hours. After cooling to room temperature, styrene (0.381 g) was added to the reaction mixture and reacted at 150° C. for 48 hours. After cooling to room temperature, the reaction mixture was poured into methanol to yield desired block copolymer having VMBTF6 and styrene (1:3) (0.755 g). The obtained block copolymer has a weight average molecular weight of 8000, a molecular weight distribution of 1.3, and excellent solubility in organic solvents, thus being useful for photochromic devices.

EXAMPLE 9

Preparation of VBMBTF6-styrene Random Copolymer

VBMBTF6-styrene random copolymer having VBMBTF6 and styrene (1:3) was prepared according to Example 7 using the diarylethene monomer (VBMBTF6) obtained in Example 3 instead of the diarylethene monomer (VMBTF6) obtained in Example 1. The obtained VBMBTF6-styrene random copolymer has a glass transition temperature of 128° C., a weight average molecular weight of 11,500, a molecular weight distribution of 1.3, and excellent solubility in organic solvents, and thus being useful for photochromic devices.

EXAMPLE 10

Preparation of VBMBTF6-styrene Block Copolymer

The diarylethene monomer (VBMBTF6; 1 g) obtained in Example 3 was dissolved in THF and the reaction flask was cooled to −78° C. to add n-butyl lithium. The reaction mixture was stirred for 4 hours and additional 1 hour at room temperature. Styrene (3 g) was added and stirred for 4 hours. Methanol was added to obtain white solids. The white solids were filtered and dried to produce desired block copolymer having VBMBTF6 and styrene (1:3) (3.1 g). The obtained block copolymer has a weight average molecular weight of 35,700, a molecular weight distribution of 1.2, and excellent solubility in organic solvents, thus being useful for photochromic devices.

Other polymers were prepared by using diarylethene monomers, comonomers, and initiators under the polymerization conditions listed in Table 2 and the properties thereof are summarized in Table 3.

TABLE 2

| | Composition (weight %) | | | | Reaction condition | |
|---|---|---|---|---|---|---|
| | Diarylethene | Comonomer | Initiator | Solvent | Reaction time (h) | Temp. (° C.) |
| Ex. 11 | VBMBTF6 (98) | — | α-tempo-phenylacetate (2) | Toluene | 72 | 130 |
| Ex. 12 | VBMBTF6 (10) | Styrene (88) | α-tempo-phenylacetate (2) | Toluene | 76 | 150 |
| Ex. 13 | VBMBTF6 (10) | Styrene (85) | n-butyl lithium (5) | THF | Same as Ex. 10 4 h/−70° C./4 h/r.t. 4 h | |
| Ex. 14 | VBMBTF6 (10) | Cyclopentadiene (85) | $SnCl_4$ + n-$Bu_4NCl$ (5) | $CH_2Cl_2$ | 10 | −78 |
| Ex. 15 | VBMBTF6 (50) | Styrene (20) Butylmethacrylate (28) | AIBN (2) | THF | 5 | 90 |

TABLE 3

| Category | Weight average molecular weight | Length of block (%)* | Distribution |
|---|---|---|---|
| Example 11 | 5200 | 100 | 1.4 |
| Example 12 | 15700 | 10 | 1.25 |
| Example 13 | 34000 | 10 | 1.1 |
| Example 14 | 7500 | 25 | 1.3 |
| Example 15 | 13500 | random | 1.26 |

*Weight % of blocks containing diarylethenes in the polymer chain measured by NMR

EXAMPLES 16–19

Preparation of Photochromic Thin Film

Example 16

VMBTF6-styrene random copolymer (0.1 g) obtained in Example 7 was dissolved in cyclohexanone (0.3 g) and stirred at room temperature for 1 hour. The mixture solution was filtered through a syringe having 0.45 μm filter and spin-coated on the surface of quartz, followed by drying in the oven at 50° C. under reduced pressure for 12 hours. The obtained thin film has excellent adhesion and high transmittance over 90%. When the thin film was irradiated with light having longer wavelength than 300 nm, it changed color to red and maintained red color when kept in a dark room. When the red colored film was irradiated with light having longer wavelength than 400 nm, it changed colorless and maintained colorless state when kept under room light. When this process was repeated, there was no phase separation. FIG. 1 shows the peak shift in the angle spectra of prism coupler upon excitation with UV and light of 633 nm for polymer film. The photo induced refractive index change was determined as 0.0030.

Example 17

A photochromic thin film having excellent adhesion and high transmittance over 90% was prepared by using diarylethene copolymer obtained in Example 8 according to the procedure of Example 16. When the obtained thin film was irradiated with light >300 nm, it changed color to red and maintained red color when kept in a dark room. When the red colored film was irradiated with light having longer wavelength than 400 nm, it changed colorless and maintained colorless state when kept under room light. When this process was repeated, there was no phase separation. The photo induced refractive index change of the film was 0.0050.

Preparation of Thin Film by Radiation Curing and Thermosetting Method

EXAMPLE 20

The compound obtained in Example 3 (10 weight %), 2,2,3,3-tetrafluoro-2,4-butylacrylated (88 weight %), and Irgacure 184 (2 weight %) were charged in a reactor and stirred at room temperature for 1 hour. The mixture was coated on the surface of quartz coated with 25 μm spacer by a bar-coating method and cured with UV light for 5 min to produce a photochromic thin film having a surface hardness of 6H or higher. A transparence of the thin film was 92% and a refractive index change was 0.0009 with UV/VIS irradiation.

EXAMPLE 21

A reaction mixture was prepared according to the procedure of Example 20 with additional adding of BPO as an initiator, coated on the surface of glass and cured in the oven at 90° C. for 5 hours to produce a photochromic film having a surface hardness of 6H or higher and a thickness of 22 μm. A transmittance of the thin film was 93% and a refractive index change was 0.0012 with UV/VIS irradiation.

EXAMPLES 22–24

Photochromic thin films were prepared by performing under the condition listed in Table 4 and the properties thereof were summarized.

TABLE 4

| | Composition of thin film | | | | Refractive |
|---|---|---|---|---|---|
| | Diarylethen monomer | Comonomer | Initiator | Curing condition | index change |
| Ex. 22 | VBMBTF6 (20) | 2,2,3,3-tetrafluoro-2,4-butyldiacrylate (78) | Irgacure 184 (2) | UV rt/5 min | 0.0015 |
| Ex. 23 | VBMBTF6 (10) | 2,2,3,3-tetrafluoro-2,4-butyldiacrylate (58) 2,2,3,3-2,3,3,3-pentafluoropropylacrylate (30) | Irgacure 784 (2) | UV rt/5 min | 0.0013 |
| Ex. 24 | 1 g (Ex. 5) (10) | 2,2,3,3-tetrafluoro-2,4-butyldiacrylate (58) 2,2,3,3-pentafluoropropylacrylate (30) | AIBN (2) | 100° C./8 hrs | 0.0013 |

Example 18

A photochromic thin film having excellent adhesion and a transmittance of higher than 90% was prepared by using diarylethene copolymer obtained in Example 9 according to the procedure of Example 16. When the obtained thin film was irradiated with light of 300 nm, it changed color to red and kept in the dark room to maintain red color. When this process was repeated, there was no phase separation.

Example 19

A photochromic thin film having excellent adhesion and a transmittance of higher than 93% was prepared by using diarylethene copolymer obtained in Example 10 according to the procedure of Example 16. When the obtained thin film was irradiated with light of 300 nm, it changed color to red and kept in the dark room to maintain red color. When this process was repeated, there was no phase separation.

COMPARATIVE EXAMPLE 1

1,2-Bis(2-methylbenzo[b]thiophene-3-yl)hexafluorocyclopentene (BTF6, 0.04 g) prepared by known method and polystyrene having a weight average molecular weight of 19300 (0.05 g) were dissolved in a mixture solution of cyclohexanone (0.3 g) and THF (0.1 g). The mixture was stirred at room temperature for 1 hour, filtered through a syringe having 0.45 μm filter and spin-coated on the surface of quartz, followed by drying in the oven at 50° C. under the pressure for 12 hours. The obtained film has low transmittance (85%) and a photo induced refractive index change of 0.0004.

Effect of the Invention

As described above, the diarylethene monomer of formula (1) of the present invention provides advantages as follows:
  1) useful for the preparation of photochromic copolymers by employing anionic initiator, cationic initiator, or radical initiator;

2) useful for the preparation of polymers having optical properties such as a narrow distribution of molecular weight (Mw/Mn<1.5) with controlling the length of blocks;

3) useful for the preparation of photochromic compositions to be used for photochromic thin films by performing thermosetting or photo irradiation; and 4) useful for the preparation of photochromic thin films having a refractive index change of 0.005 with light irradiation. Particularly, the diarylethene monomer of formula (1) can be used for the preparation of styrene base copolymers, block copolymers, hyper branched copolymers or graft copolymers. Further, optical properties such as refractive index can be controlled by adjusting the amount of each component within appropriated range depending the purpose and required property of the product.

Still further, the diarylethene monomer is applicable for optical applications such as optical lenses, filter, imaging, large scale integrated devices, optical switches, optical disk and optical recording mediums. The photochromic products prepared by using diarylethene compounds have excellent transparence, refractive index, hardness, scratch resistance, heat stability and repetitive durability and especially direct image recording-erasing by light irradiation with excellent storage stability.

What is claimed is:

1. A diarylethene monomer of the formula (1),

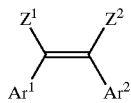
(1)

wherein $Z^1$ and $Z^2$ are (a) each a independently cyano group or (b) chemically linked together to form a 4–6-membered ring, the ring being optionally substituted with one or more fluoro atoms; and $Ar^1$ and $A^2$ are independently

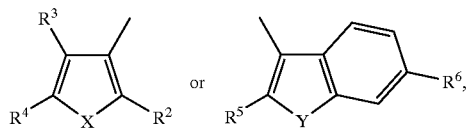

where X and Y are independently O, S, NH or N—OH$_3$; $R^2$ and $R^5$ are independently optionally substituted $C_1$–$C_3$ alkyls; $R^3$ is H, F or optionally substituted $C_1$–$C_3$ alkyls; $R^4$ and $R^6$ are independently H, CH$_3$, C(=O)CH$_3$, isoxazole, vinyl, C(=O)—Ar$^3$—CH=CH$_2$, C(=O)—Ar$^4$, or N(Ar$^5$)$_2$, with the proviso that at least one of $Ar^1$ or $Ar^2$ comprises $R^4$ or $R^6$ chosen from vinyl or C(=O)—Ar$^3$—CH=CH$_2$, and $Ar^3$, $Ar^4$ or $Ar^5$ are optionally substituted benzenes or thiophenes.

2. A photochromic polymer prepared by polymerizing the diarylethene monomer of formula (1),

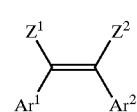
(1)

wherein $Z^1$, $Z^2$, $Ar^1$ and $Ar^2$ areas defined as in claim 1.

3. The photochromic polymer according to claim 2, wherein said polymer is diarylethene homopolymer, diarylethene copolymer, diarylethene random copolymer, or diarylethene block copolymer.

4. A photochromic polymerizable composition comprising:

0.01–99.8 weight % of a diarylethene monomer of formula (1),

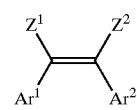
(1)

wherein $Z^1$ and $Z^2$ are (a) each a cyano group or (b) chemically linked together to form a 4–6-membered ring, the ring being optionally substituted with one or more fluoro atoms; and $Ar^1$ and $Ar^2$ are independently

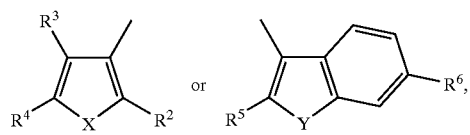

where X and Y are independently O, S, NH or N—CH$_3$; $R^2$ and $R^5$ are independently optionally substituted $C_1$–$C_3$ alkyls; $R^3$ is H, F or optionally substituted $C_1$–$C_3$ alkyl; $R^4$ and $R^6$ are independently H, CH$_3$, C(=O)CH$_3$, isoxazole, vinyl, C(=O)—Ar$^3$—CH=CH$_2$, C(=O)—Ar$^4$, or N(Ar$^5$)$_2$, with the proviso that at least one of $Ar^1$ or $Ar^2$ comprises $R^4$ or $R^6$ chosen from vinyl or C(=O)—Ar$^3$—CH=CH$_2$, and $Ar^3$, $Ar^4$ or are optionally substituted benzenes or thiophenes;

0–99.8 weight % of at least one comonomer having unsaturated functional group chosen from styrene, vinyl, methacryl and acryl compound;

and 0.19–5 weight % of a polymerization initiator.

5. The photochromic polymerizable composition according to claim 4, wherein said polymerization initiator is chosen from at least one of a cationic initiator, an ionic initiator, and radical initiator.

6. A photochromic thin film prepared by using the photochromic polymerizable composition in claim 4.

* * * * *

UNITED STATES PATENT AND TRADEMARK OFFICE
CERTIFICATE OF CORRECTION

PATENT NO. : 6,787,621 B2
DATED : September 7, 2004
INVENTOR(S) : Eunkyoung Kim et al.

It is certified that error appears in the above-identified patent and that said Letters Patent is hereby corrected as shown below:

Title page,
Item [75], Inventors, "Choongchungnam-do" should read -- Seoul --;

Column 17,
Line 37, delete "independently";
Line 41, "$A^2$" should read -- $Ar^2$ --;
Line 50, "$N-OH_3$" should read -- $N-CH_3$ --;

Signed and Sealed this

First Day of February, 2005

JON W. DUDAS
*Director of the United States Patent and Trademark Office*